US012760349B2

(12) United States Patent
Cha et al.

(10) Patent No.: US 12,760,349 B2

(45) Date of Patent: Oct. 13, 2026

(54) FGF21 PRODUCTION METHOD USING THERMOELASTICITY OF FGF21

(71) Applicant: TODD PHARM CO., LTD., Seoul (KR)

(72) Inventors: Sun-Shin Cha, Seoul (KR); Soo-Bong Park, Seoul (KR); Ye-Eun Jung, Seoul (KR); Da-Woon Bae, Seoul (KR); Bo-Gyeong Jeong, Seoul (KR); Bu-Gyeong Kang, Seoul (KR); Jung-hyun Lee, Busan (KR); Hyung-Soon Yim, Seoul (KR); Kyeong Won Lee, Busan (KR); Young Jun An, Ansan (KR)

(73) Assignee: TODD PHARM CO., LTD., Seoul (KR)

( * ) Notice: Subject to any disclaimer, the term of this patent is extended or adjusted under 35 U.S.C. 154(b) by 518 days.

(21) Appl. No.: 18/035,087

(22) PCT Filed: Sep. 27, 2021

(86) PCT No.: PCT/KR2021/013090

§ 371 (c)(1),
(2) Date: May 2, 2023

(87) PCT Pub. No.: WO2022/097914

PCT Pub. Date: May 12, 2022

(65) Prior Publication Data

US 2024/0271174 A1 Aug. 15, 2024

(30) Foreign Application Priority Data

Nov. 3, 2020 (KR) ........................ 10-2020-0145101

(51) Int. Cl.
*C12P 21/02* (2006.01)
*C07K 14/50* (2006.01)

(52) U.S. Cl.
CPC .............. *C12P 21/02* (2013.01); *C07K 14/50* (2013.01)

(58) Field of Classification Search
CPC ........... C12P 21/02; C07K 14/50; C07K 1/14; C07K 1/36
See application file for complete search history.

(56) References Cited

U.S. PATENT DOCUMENTS

| | | | | |
|---|---|---|---|---|
| 2010/0285131 A1* | 11/2010 | Belouski | A61P 3/00 | 514/6.9 |
| 2013/0085098 A1* | 4/2013 | Dickinson | A61P 3/06 | 514/6.9 |

FOREIGN PATENT DOCUMENTS

| | | | |
|---|---|---|---|
| CN | 106220724 | A | 12/2016 |
| CN | 110791517 | A | 2/2020 |
| KR | 10-2014-0059271 | A | 5/2014 |
| KR | 10-2015-0006060 | A | 1/2015 |
| KR | 10-2018-0083938 | A | 7/2018 |
| WO | 2013052311 | A1 | 4/2013 |
| WO | 2013188181 | A1 | 12/2013 |
| WO | 2017093465 | A1 | 6/2017 |
| WO | 2018196616 | A1 | 11/2018 |

OTHER PUBLICATIONS

LaVallie ER et al. Thioredoxin as a Fusion Partner for Production of Soluble Recombinant Proteins in *Escherichia coli*. 2000. Methods in Enzymology. vol. 326, p. 322-340. (Year: 2000).*
KIPO, Application No. PCT/KR2021/013090, International Search Report dated Jan. 14, 2022.
McCoy, John et al., "Expression and Purification of Thioredoxin Fusion Proteins," Current Protocols in Molecular Biology, 1994, Unit 16.8, 14 pages.
KIPO, Application No. KR10-2020-0145101, Request for the Submission of an Opinion dated Apr. 26, 2022.
KIPO, Application No. KR10-2020-0145101, Written Decision on Registration dated Dec. 12, 2022.

* cited by examiner

*Primary Examiner* — Paul J Holland
(74) *Attorney, Agent, or Firm* — Fitch, Even, Tabin & Flannery LLP

(57) ABSTRACT

The present application relates to a method of producing or purifying an FGF21 protein by using the heat-elasticity of FGF21.
The method of producing or purifying the FGF21 protein according to an embodiment of the present application utilizes the heat stability and heat-elasticity of the FGF21 protein that is not denatured or precipitated even upon heat treatment and returns to the original structure when re-cooled after heat treatment, resulting in advantages of improving efficiency by simplifying a protein production process.

8 Claims, 12 Drawing Sheets

Specification includes a Sequence Listing.

FIG. 1

SEQUENCE INFORMATION OF FGF21(Signal peptide/29~209aa/41~173aa)

MDSDE TGFEH SGLWV SVLAG LLLGA CQAHP IPDSS PLLQF GGQVR QRYLY
TDDAQ QTEAFI LEIRE DGTYG GAADQ SPESL LQLKA LKPGY IQILG VKTSR
FLCQR PDGAL YGSLH FDPEA CSFRE LLLED GYNVY QSEAH GLPLH LPGNK
SPHRD PAPRG PARFL PLPGL PPALP EPPGI LAPQP PDVGS SDPLS MVGPS
QGRSP SYAS
(SEQ ID NO: 4)

FIG. 2

M Unboiled Boiled

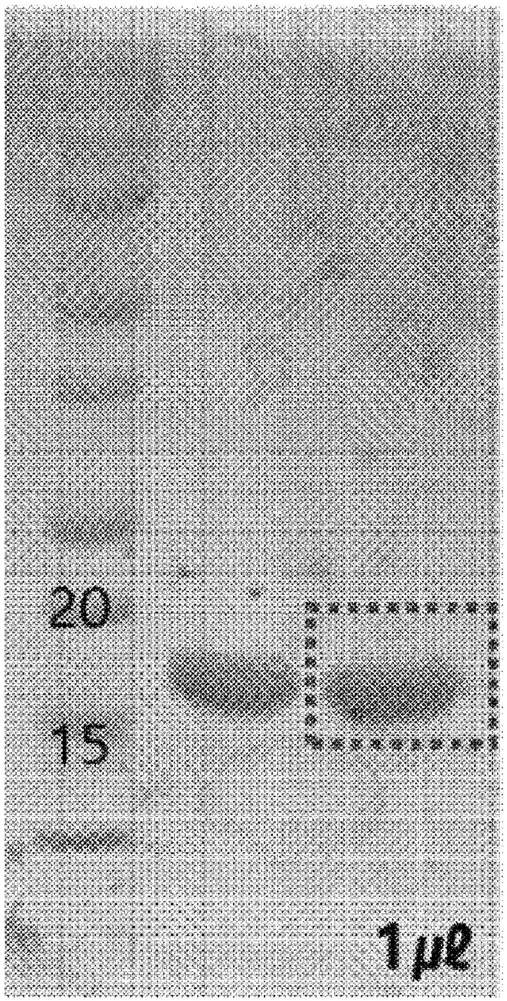

> un boiled

Protein sequence coverage: 69%

Matched peptides shown in *bold*

1 GGQVRQRYLY TDDAQQTEAH LEIREDGTVG GAADQSPESL LQLKALKPGV
51 IQILXGVKTS RFLCQRPDGA LYGSLHFDPE ACSFRELLLE DGYNVYQSEA
101 HGLPLHLPGN KSPHRDPAPR GPARFLPLPG LPPALPEPPG ILAPQPPDVG
151 SSD (SEQ ID NO: 5)

peptide tolerance : 30ppm, miss cleavage : 1
When raised to 50 ppm, the coverage is 71 % as below > boiled Protein sequence coverage: 71%

Matched peptides shown in *bold*

1 GGQVRQRYLY TDDAQQTEAH LEIREDGTVG GAADQSPESL LQLKALKPGV
51 IQILXGVKTS RFLCQRPDGA LYGSLHFDPE ACSFRELLLE DGYNVYQSEA
101 HGLPLHLPGN KSPHRDPAPR GPARFLPLPG LPPALPEPPG ILAPQPPDVG
151 SSD (SEQ ID NO: 5)

peptide tolerance : 30ppm, miss cleavage : 1

FIG. 6
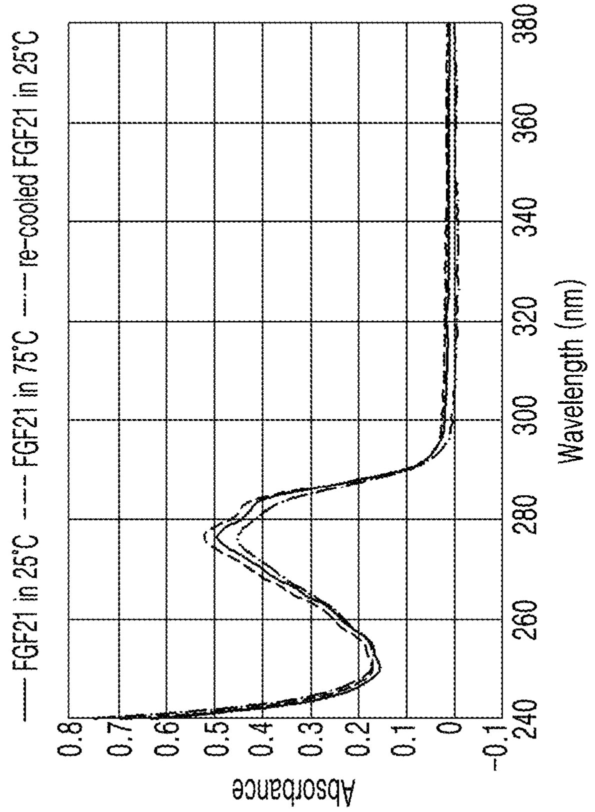
| Condition | $OD_{280nm}$ | $OD_{350nm}$ | A.I. |
|---|---|---|---|
| 25°C | 0.4472 | 0.0152 | 3.52 |
| 75°C | 0.4717 | 0.0178 | 3.92 |
| Re-cooled 25°C | 0.4179 | −0.0012 | −0.29 |
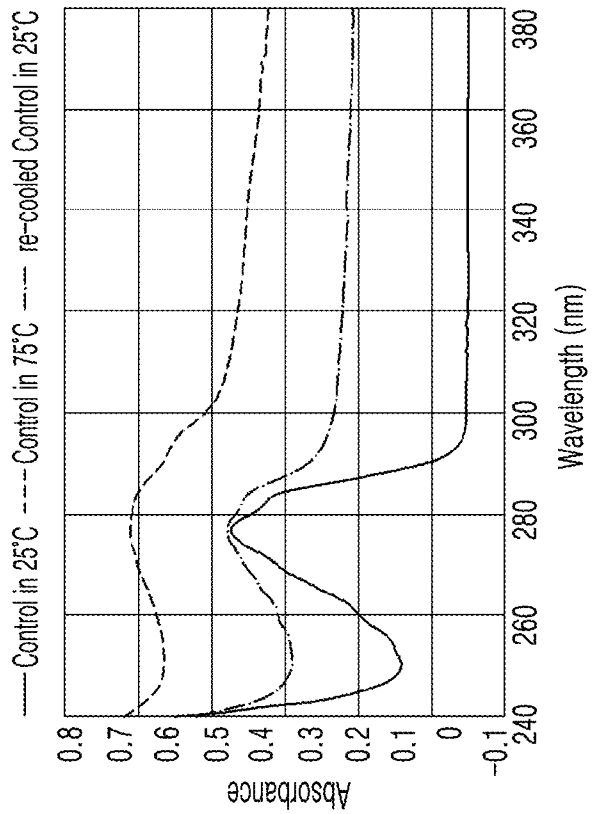
| Condition | $OD_{280nm}$ | $OD_{350nm}$ | A.I. |
|---|---|---|---|
| 25°C | 0.5936 | −0.001 | −0.168 |
| 75°C | 0.9201 | 0.5871 | 176.3 |
| Re-cooled 25°C | 0.6367 | 0.3285 | 106.6 |

<Far-UV CD spectrum of hFGF21>

0.1mg/ml, 5℃/min, path length = 1mm, in PBS bfr

<Near-UV CD spectrum of hFGF21>

5mg/ml, 5°C/min, path length = 1mm, in PBS bfr

FGF21 PRODUCTION METHOD USING THERMOELASTICITY OF FGF21

CROSS-REFERENCE TO RELATED APPLICATIONS

This application is a U.S. national phase application filed under 35 U.S.C. § 371 of International Application No. PCT/KR2021/013090, filed Sep. 27, 2021, which is based upon and claims the benefit of priority from prior Korean Application No. 10-2020-0145101, filed Nov. 3, 2020.

REFERENCE TO A SEQUENCE LISTING

The Sequence Listing associated with this application is filed in electronic format via EFS-Web and is hereby incorporated into the specification in its entirety. The name of the text file containing the Sequence Listing is "GN-68197-US_amended sequence listing". The size of the text file is 7.39 KB, and the file was created on Feb. 20, 2026.

TECHNICAL FIELD

The present application relates to a method of producing or purifying an FGF21 protein using heat-elasticity of FGF21.

BACKGROUND ART

A mammalian-derived fibroblast growth factor (FGF) is a protein that regulates glucose/lipid metabolism, cell differentiation and proliferation, etc., by binding to an ectodomain of a receptor present in cell membrane and activating a tyrosine kinase domain of the receptor present in cytoplasm. The FGF family consists of 22 proteins that are structurally similar, and is divided into 7 subfamilies. FGFs of five subfamilies (i.e., FGF1, FGF4, FGF7, FGF8, and FGF9 subfamilies) require heparin or heparan sulfate to bind with FGFR. Heparin/heparan sulfate is a negatively charged polysaccharide, which belongs to the Glycosaminoglycan (GAG) family, interacts with a variety of proteins to regulate numerous functions on both the cell surface and extracellular matrix. FGFs exhibit high affinity for heparin/heparan sulfate, allowing them to function as paracrine that remain in close proximity to the cells that secrete them.

FGF21 belongs to the endocrine subfamily (FGF19 subfamily) that includes FGF23 and FGF15/19. FGF21 is a major endogenous agonist of the FGF21 receptor, consisting of co-receptors FGF receptor 1c and β-Klotho.

FGF21 has recently been widely studied as an active ingredient in various therapeutic agents. In detail, in July 2019, Yuhan Corporation signed a license agreement with Boehringer Ingelheim, a multinational pharmaceutical company in Germany, for the purpose of developing a therapeutic agent for nonalcoholic steatohepatitis (NASH), and such a therapeutic agent is a dual agonist, in which FGF21 and glucagon-like peptide-1 (GLP-1) are fused. Currently, nonclinical toxicity test studies have been completed for the substance, and it is known that joint research is underway with the goal of clinical entry. In addition, MERCK, a multinational pharmaceutical company, is also developing MK-3655, a monoclonal antibody therapeutic agent that acts on the β-Klotho/FGFR1c composite, for the purpose of treatment of NASH. In this regard, it is known that FGF21 is a new drug candidate substance bringing attention in domestic and international pharmaceutical markets as a therapeutic agent for diabetes and NASH.

In addition, as various pharmacological effects on the brain, bone, pancreas, liver, etc. upon the FGF21 administration have been studied, the scope of application of a therapeutic agent including FGF21 as an active ingredient is expected to gradually expand.

Accordingly, the present inventors have made efforts to develop a method of efficiently purifying and producing the FGF21 protein, and as a result, it is confirmed that the FGF21 protein is not denatured even when a temperature higher than the general protein denaturation temperature is applied, and the physiological activity thereof is also maintained. Using this, a method of producing FGF21 protein is developed and the disclosure was completed.

DISCLOSURE

Technical Problem

The disclosure relates to a method of producing FGF21 protein, the method comprising: a) culturing a transformant that produces a FGF21 protein; and b) heating the transformant or culture medium to a temperature of 40° C. or higher.

However, the problem to be solved by the disclosure is not limited to the above-mentioned problem, and other problems not mentioned will be clearly understood by those skilled in the art from the description below.

Technical Solution

A first aspect of the disclosure provides a method of producing FGF21 protein, the method comprising: a) culturing a transformant that produces a FGF21 protein; and b) heating the transformant or culture medium to a temperature of 40° C. or higher.

A second aspect of the disclosure provides a method of purifying FGF21 protein, the method comprising heating a mixture containing FGF21 protein and impurities at a temperature of 40° C. or higher.

Advantageous Effects

In the method of producing or purifying the FGF21 protein according to an embodiment of the disclosure, the heat stability and heat-elasticity of FGF21 protein that does not denature or precipitate even after heat treatment and returns to the original structure when re-cooled is used, resulting in advantages of improving efficiency by simplifying a protein production process.

DESCRIPTION OF DRAWINGS

FIG. 1 is a diagram showing information of the amino acid sequences of an FGF21 protein (SEQ ID NO: 4).

FIG. 2 is a diagram showing results of SDS-PAGE and MASS analysis (SEQ ID NO: 5) of the supernatant portion after heat treatment of an FGF21 protein.

FIG. 6 is a diagram showing aggregation index results after heat treatment and re-cooling of an FGF21 protein.

BEST MODE

Figure 3:
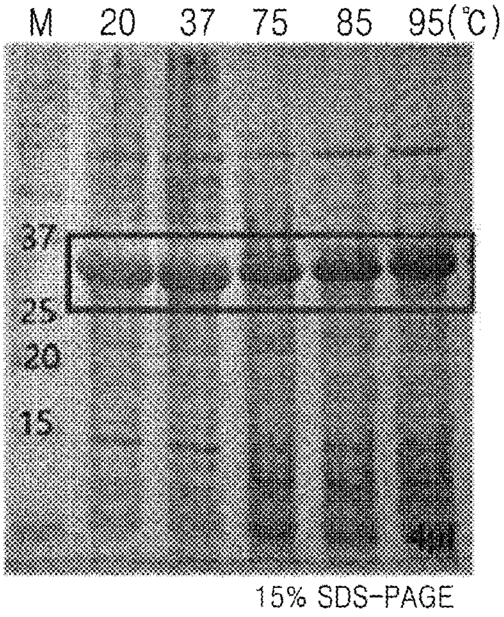
FIG. 3 is a diagram showing SDS-PAGE results after heat treatment of a FGF21 terminal-truncation mutant at various temperatures.

Hereinafter, with reference to the accompanying drawings, embodiments of the present application will be described in detail so that those skilled in the art to which the present application pertains may readily practice the present application. However, the present application may be implemented in various different forms, and is not limited to embodiments described herein. In addition, to clearly describe the present application, parts unrelated to the description of the present application are omitted in the drawings, and like elements are denoted by like reference numbers throughout the specification.

Throughout the specification of the present application, when a portion is said to be "connected" to another portion, this includes not only cases where these portions are "directly connected" to each other, but also cases where these portions are "indirectly connected" through other materials such as a linker therebetween.

Throughout the specification of the present application, when a portion is said to "include" an element, this does not mean that the portion excludes other elements, but rather may include other elements, unless specifically stated otherwise. As used throughout the specification of the present application, the terms "about," "substantially," and the like are used to denote values that are within or close to the specified range when manufacturing and material tolerances inherent to the mentioned meaning are given, and are intended to prevent unscrupulous infringers from improperly exploiting disclosures that mention precise or absolute values stated to aid understanding of the present application. As used throughout the specification of the present application, the term "step of (~ing)" or "~ step" does not mean "step for ~."

Throughout the specification of the present application, the term "combination(s) thereof" included in the Makushi-format expression refers to a mixture or combination of one or more selected from the group consisting of elements described in the Makushi-format expression, and refers to inclusion of one or more selected from the group consisting of the elements.

Throughout the specification of the present application, the expression "A and/or B" refers to "A or B or A and B".

Hereinafter, embodiments and examples of the present application will be described in detail with reference to the accompanying drawings. However, the present application is not limited to these embodiments, examples, and drawings.

A first aspect of the present application provides a method of producing an FGF21 protein, the method including: a) culturing a transformant producing an FGF21 protein; and b) heating the transformant or culture medium at a temperature of 40° C. or higher.

As used throughout the specification of the present application, the term "fibroblast growth factor 21 (FGF21)" is a protein consisting of 209 amino acids. In a mature form (29-209aa) which lacks a signal peptide (1-28aa), it differs from paracrine FGF proteins in that it has low binding affinity for heparin/heparan sulfate, enabling it to travel through the bloodstream beyond the vicinity of the secreting cells. Due to these characteristics, FGF21 functions as an endocrine hormone that reaches a distant target and exerts its physiological activity. FGF21 acts by forming a complex with FGFR1c, which is one of FGF receptors present on the cell surface, and the cofactor β-Klotho protein at the same time. Heparin/heparan sulfate may be present in all types of cells, whereas β-Klotho may be mainly distributed in the adipose tissue, the liver, and the pancreas. Therefore, FGF21 may affect the activity of cells expressing FGFR1c and β-Klotho, thereby regulating glucose and lipid metabolism. For example, FGF21 has been reported to be effective in improving metabolic diseases such as type 2 diabetes and fatty liver diseases. In particular, FGF21 is emerging as a key candidate substance for drug development targeting lipid metabolism disorders such as non-alcoholic fatty liver disease and non-alcoholic steatohepatitis.

In an embodiment of the present application, the FGF21 protein may be a wild-type or a variant, and the wild-type or the variant may include the amino acid sequence of SEQ ID NO: 2. In an embodiment of the present application, the FGF21 protein may include a peptide including one or more of the amino acid sequences of SEQ ID NOs: 1 to 3, and specifically may include the amino acid sequence of SEQ ID NO: 2. More specifically, the variant may be one in which the N- and C-termini are removed from the wild-type FGF21 protein consisting of the amino acid sequence of SEQ ID NO: 1.

In an embodiment of the present application, it was confirmed that, when including a peptide of SEQ ID NO: 2 consisting of the $41^{st}$ to the $173^{rd}$ amino acids of FGF21, which is expected to have a beta (3)-trefoil body structure, the peptide does not denature or precipitate even at temperatures of about 100° C. or higher, and that the original protein structure is maintained upon re-cooling after heat treatment. In such re-cooling, it was confirmed that the physiological activity of FGF21 was also maintained, indicating excellent heat stability/heat-elasticity.

In another embodiment of the present application, it is confirmed that, even when some N- and C-terminal sequences are removed from the wild-type FGF21 (29-209aa), excellent heat stability/heat-elasticity is maintained as long as the β-trefoil body structure (41-173aa) is preserved.

In an embodiment of the present application, the transformant may include a polynucleotide encoding the FGF21 protein, and specifically may include a gene construct or recombinant vector including the polynucleotide encoding the FGF21 protein.

In an embodiment of the present application, the transformant producing the FGF21 protein may include a gene construct or recombinant vector including the polynucleotide encoding the FGF21 protein, enabling expression of FGF21.

As used throughout the specification of the present application, the term "recombinant vector" refers to a vector capable of expressing a peptide or protein encoded by a foreign nucleic acid inserted into the vector, preferably referring to a vector designed to include the polynucleotide encoding the FGF21 protein. The "vector" refers to any medium for introducing and/or transferring nucleotides into a host cell in vitro, ex vivo, or in vivo, and may be a replicon capable of binding to other DNA fragments and inducing replication of the bound fragments. The "replicon" refers to any genetic unit (e.g., a plasmid, a phage, a cosmid, a chromosome, a virus, etc.) that functions as an autonomous unit for DNA replication within a living organism, i.e., a genetic unit capable of replication through its own regulation.

In the present application, the recombinant vector or recombinant expression vector may preferably include a promoter as a transcription initiation factor to which RNA polymerase binds, any operator sequence for regulating transcription, a sequence encoding an appropriate mRNA ribosome-binding site and a sequence regulating termination of transcription and translation, a terminator, and the like, more preferably, may further include a gene in the 5'UTR of M17 for increasing protein synthesis, an HDEL gene for minimizing protein degradation to stably maintain proteins within the endoplasmic reticulum, and the like, and more preferably, may include a gene for tagging to increase the yield of recombinant proteins, a gene for tagging to maintain the structural stability of recombinant proteins, a gene for tagging to easily separate recombinant proteins, a marker gene for selecting antibiotic resistance genes for screening a transformant, and the like. Representative tags for the easy separation Avi tag, Calmodulin tag, polyglutamate tag, E tag, FLAG tag, HA tag, His tag, Myc tag, S tag, SBP tag, IgG-Fc tag, CTB tag, Softag 1 tag, Softag 3 tag, Strep tag, TC tag, V5 tag, VSV tag, Xpress tag, and the like. Representative marker genes for the screening may include a herbicide-resistance gene, such as glyphosate or phosphinothricin, an antibiotic-resistance gene, such as kanamycin, G418, bleomycin, hygromycin, and chloramphenicol, aadA gene, and the like. Representative promoters may include pEMU promoter, MAS promoter, histone promoter, Clp promoter, cauliflower mosaic virus-derived 35S promoter, cauliflower mosaic virus-derived 19S RNA promoter, plant actin protein promoter, ubiquitin protein promoter, cytomegalovirus (CMV) promoter, simian virus 40 (SV40) promoter, respiratory syncytial virus (RSV) promoter, elongation factor-1 alpha (EF-1α) promoter, and the like. Representative terminators may include nopaline synthase (NOS), rice amylase RAmyl A terminator, phaseoline terminator, a terminator for Octopine gene of *Agrobacterium tumefaciens*, an rrnB1/B2 terminator of *Escherichia coli*, and the like. However, the type of additional genes to be inserted is not limited as long as it is already used in the production of recombinant proteins.

As used throughout the specification of the present application, the term "transformation" refers to the overall change in the genetic properties of an organism caused by introduction of DNA, and the term "transformant or transgenic organism" refers to a living organism produced by introducing a foreign gene through molecular genetic methods, and may preferably be a living organism transformed by the recombinant expression vector of the present disclosure, wherein the living organism is not limited if it is a living creature, and may include a microorganism, a eukaryotic cell, an insect, an animal, a plant, and the like, and may preferably include *E. coli, Salmonella, Bacillus*, yeast, an animal cell, a mouse, a rat, a dog, a monkey, a pig, a horse, a cow, *A. tumefaciens*, a plant, and the like, but the living organism is not limited thereto. The transformant may be prepared by the means of transformation, transfection, *Agrobacterium*-mediated transformation, particle gun bombardment, sonication, electroporation, polyethylene glycol (PEG)-mediated transformation, and the like, and there is no limitation on methods as long as the vector of the present application may be introduced.

In an embodiment of the present application, the FGF21 protein may be heat-stable or heat-elastic.

As used throughout the specification of the present application, the term "heat stability" refers to the characteristic whereby, even when subjected to heat exceeding a certain level under heat treatment conditions, proteins do not undergo denaturation or precipitation, and the physiological activity of proteins remains unchanged or unmodified, maintaining the original characteristics/functions identical or similar to those prior to heat treatment.

In an embodiment of the present application, when the FGF21 protein is heat-treated, a control group using general proteins showed denaturation and precipitation. However, the FGF21 protein showed no denaturation or precipitation even after heat treatment at temperatures of about 100° C. or higher, and its physiological functions, such as FGFR1c receptor activity and the like, were confirmed to be maintained, demonstrating that the FGF21 protein has heat stability.

As used throughout the specification of the present application, the term "heat-elasticity" refers to the property that, after being subjected to heat above a certain level under heat treatment conditions and then re-cooled, a protein recovers its original characteristics/functions to a state identical or similar to that before heat treatment.

In an embodiment of the present application, after heat treatment followed by re-cooling of the FGF21 protein, it was confirmed that the FGF21 protein retains its original characteristics and functions, indicating that the FGF21 protein has heat-elastic characteristics.

In an embodiment of the present application, the FGF21 protein may have a β-trefoil structure.

As used throughout the specification of the present application, the term "β-trefoil" or "β-trefoil fold" structure refers to a protein folding structure consisting of six B hairpins, each formed by two β strands. Such a structure forms a β barrel with a triangular "cap" consisting of three hairpins, and accordingly, has an approximate three-fold symmetry.

In an embodiment of the present application, the method may include heating the transformant or culture medium to a temperature that is higher than a temperature at which general proteins may denature. Specifically, the temperature may be about 40° C. or higher, about 45° C. or higher, about 50° C. or higher, about 55° C. or higher, about 60° C. or higher, about 65° C. or higher, about 70° C. or higher, about 75° C. or higher, about 80° C. or higher, about 85° C. or higher, about 90° C. or higher, about 95° C. or higher, or about 100° C., and more specifically, may be about 40° C. to about 300° C., about 40° C. to about 250° C., about 40° C. to about 200° C., about 40° C. to about 150° C., about 40° C. to about 120° C., about 50° C. to about 300° C., about 50° C. to about 250° C., about 50° C. to about 200° C., about 50° C. to about 150° C., about 50° C. to about 120° C., about 60° C. to about 300° C., about 60° C. to about 250° C., about 60° C. to about 200° C., about 60° C. to about 150° C., about 60° C. to about 120° C., about 70° C. to about 300° C., about 70° C. to about 250° C., about 70° C. to about 200° C., about 70° C. to about 150° C., about 70° C. to about 120° C., about 80° C. to about 300° C., about 80° C. to about 250° C., about 80° C. to about 200° C., about 80° C. to about 150° C., about 80° C. to about 120° C., about 90° C. to about 300° C., about 90° C. to about 250° C., about 90° C. to about 200° C., about 90°

C. to about 150° C., or about 90° C. to about 120° C., but the temperature is not limited thereto.

In an embodiment of the present application, the FGF21 protein may be additionally fused to a thermostable protein tag.

In an embodiment of the present application, the thermostable protein tag may be linked to the N-terminus or C-terminus of the FGF21 protein, and is not limited thereto as long as it may enhance the production/purification efficiency of the FGF21 protein without affecting the characteristics/functions of the protein.

In an embodiment of the present application, the thermostable protein tag is a heat-resistant protein tag that does not denature when heated, and may include one or more selected from the group consisting of heat-stable proteins including a protein derived from thermophilic organisms, thioredoxin (Trx), and DNAK.

In an embodiment of the present application, the FGF21 protein and the protein tag may be directed connected to each other or connected to each other via a linker. The linker is not specifically limited as long as it does not affect the characteristics/functions of the FGF21 protein or a fusion protein with the protein tag attached thereto. For example, the linker may consist of a nucleic acid or a peptide.

In an embodiment of the present application, the linker may be cleaved or decomposed by various biological or chemical actions, such as enzymatic actions within or outside the cell. Specifically, the cleavage may be done by protease treatment using, as a linker, a specific sequence recognized by proteases such as tobacco etch virus (TEV) protease, thrombin, factor Xa, and the like. Alternatively, the cleavage may be done by using a linker consisting of asparagine-glycine (Asn-Gly) and performing heat treatment (40° C. to 42° C., 3 hours) utilizing hydroxylamine ($NH_2OH$).

In an embodiment of the present application, the culturing of the transformant may be, although not particularly limited thereto, performed by a batch culture method, a continuous culture method, and a fed-batch culture method known in the art. Here, the culture conditions, although not particularly limited thereto, may involve use of a basic compound (e.g., sodium hydroxide, potassium hydroxide, or ammonia) or an acidic compound (e.g., phosphoric acid or sulfuric acid) to adjust the pH to an appropriate level (e.g., pH of about 5 to about 9, specifically, pH of about 6 to 8, more specifically, pH of 6.8), and introduction of oxygen or an oxygen-containing gas mixture into the culture medium to maintain aerobic conditions. The culture temperature may be maintained at about 20° C. to about 45° C., specifically, about 25° C. to about 40° C., and the culturing may be performed for about 10 hours to about 160 hours. The FGF21 protein produced by the culturing may be secreted into the medium or may remain within the transformant.

Furthermore, a medium used in the culturing may be supplemented with a carbon source, such as sugar and carbohydrate (e.g., glucose, sucrose, lactose, fructose, maltose, molasse, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid), individually or in combination. However, the carbon source is not limited thereto. As a nitrogen source, a nitrogen-containing organic compound (e.g., peptone, yeast extract, meat extract, malt extract, corn steep liquor, soybean meal powder, and urea) or an inorganic compound (e.g., ammonium sulfate, ammonium chloride, ammonium phosphate, ammonium carbonate, and ammonium nitrate) may be used individually or in combination. However, the nitrogen source is not limited thereto. As a phosphorus source, potassium dihydrogen phosphate, dipotassium hydrogen phosphate, and corresponding sodium-containing salts may be used individually or in combination. However, the phosphorus source is not limited thereto, and other essential growth-promoting substances, such as metal salts (e.g., magnesium sulfate or iron sulfate), amino acids, and vitamins may be used.

In an embodiment of the present application, the method may further include (c) removing proteins denatured by heat treatment.

In an embodiment of the present application, the removing of the proteins that have been denatured may involve precipitating the denatured proteins, specifically, the proteins derived from the transformant, through centrifugation, and then removing precipitates. In this process, the FGF21 protein that has not been denatured even after heat treatment may be present in a supernatant fraction after the centrifugation, allowing it to be easily obtained.

In an embodiment of the present application, the method may further include recovering the produced FGF21 protein. The recovering may involve recovering from cultured cells or a supernatant thereof, and those skilled in the art may select an appropriate process for the recovery. The recovering of the FGF21 protein produced in the culturing of the present application may involve collecting the desired product from the culture medium by using a suitable method known in the art, depending on a culture method, such as batch, continuous, or fed-batch culture methods.

In an embodiment of the present application, the recovering of the FGF21 protein may involve removing proteins other than the FGF21 protein (proteins derived from the transformant) that precipitate upon denaturation by heat treatment by centrifugation, thereby obtaining only the FGF21 protein that remains undenatured due to its heat stability (heat-elasticity) despite the heat treatment.

A second aspect of the present application provides a method of purifying an FGF21 protein, the method comprising heating a mixture containing an FGF21 protein and impurities at a temperature of 40° C. or higher.

Contents overlapping with the first aspect also apply to the method of the second aspect.

In an embodiment of the present application, the impurities may include proteins other than the FGF21 protein produced during the FGF21 protein production process, and specifically may include proteins derived from the transformant producing the FGF21 protein.

In an embodiment of the present application, the purifying of the FGF21 protein may involve removing impurities (proteins derived from the transformant) that precipitate upon denaturation by heat treatment by centrifugation, thereby obtaining only the FGF21 protein that remains undenatured due to its heat stability (heat-elasticity) despite the heat treatment.

Hereinafter, the present disclosure will be described in greater detail through the following examples of the present application. However, these examples are merely illustrative to aid in understanding the present application and contents of the present application are not limited thereto.

MODE FOR INVENTION

Examples

Example 1: Confirmation of Heat-Elasticity of FGF21

Recently, a specific reaction to heat of fibroblast growth factor 21 (FGF21), which is widely known as a protein drug candidate, was discovered, and an FGF21 purification technology was developed using this reaction. In the case of general proteins, a denaturation phenomenon in which tertiary structures of proteins are unfolded is observed at a temperature above certain temperatures. Denatured proteins not only lose the activity, but also aggregate and precipitate. However, in the case of FGF21, it was observed that denaturation and precipitation did not occur even at a high temperature of about 100° C. In addition, it was observed that the structure of FGF21 continuously changes as the temperature increases, but returns to the original structure upon re-cooling and maintains the physiological activity.

In particular, it was confirmed that these characteristics are maintained as long as the β-trefoil body structure (41-173aa) is preserved, even when some of the N-terminal or C-terminal sequences are removed from wild-type FGF21 (29-209aa) in the mature form. Such maintenance was confirmed on the basis of the structure modeled through the secondary and tertiary structure prediction programs and through the fact that the biochemical and physiological properties of the wild type were experimentally the same as those of terminal-truncated variants. The sequence information of FGF21 is shown in FIG. 1 and Table 1 below. In addition, the specific heat stability/heat reactivity of FGF21 was named heat-elasticity.

TABLE 1

| | Name | | Sequence | SEQ ID NO. |
|---|---|---|---|---|
| Human FGF21 | Wild type, mature type | | 29-209 | 1 |
| | Terminal-truncated variant | □ ΔN12ΔC36 | 41-173 | 2 |
| | | ②□ □ N4 | 33-209 | 3 |

To confirm the heat stability of the FGF21 protein, the following experiment was performed to observe whether denaturation or precipitation occurs after heat was applied to FGF21, which has been already purified to a high purity of 90% or more at room temperature without heat treatment.

First, the FGF21 (15 mg/ml, 41-192aa) purified to a high purity of 90% or more at room temperature without heat treatment was incubated at 100° C. for 1 hour, followed by centrifugation. After separation into a supernatant fraction and a pellet fraction, SDS-PAGE analysis was performed on each fraction. As a result, FGF21 was found only in the supernatant fraction, and the protein of the corresponding gel was identified to be FGF21 by mass analysis on the corresponding gel (FIG. 2). Referring to the results above, it was confirmed that denaturation and precipitation did not occur in the FGF21 protein even after heat treatment.

Next, the terminal-truncated mutant (1), which is expected to form a β-trefoil structure, was expressed through an *E. coli* system in the form of a heat-resistant Trx-tag fusion. After cell lysis, a supernatant fraction separated by centrifugation was incubated for 10 minutes at 5 different temperatures. To separate water-insoluble proteins denatured and precipitated by heat treatment, centrifugation (at 14.000 rpm for 20 minutes) was performed again, and as a result of identifying a supernatant fraction thus obtained by SDS-PAGE, it was confirmed that the terminal-truncated variant (1) exists in a water-soluble state in spite of strong heat treatment at 95° C. (FIG. 3).

Figure 4:
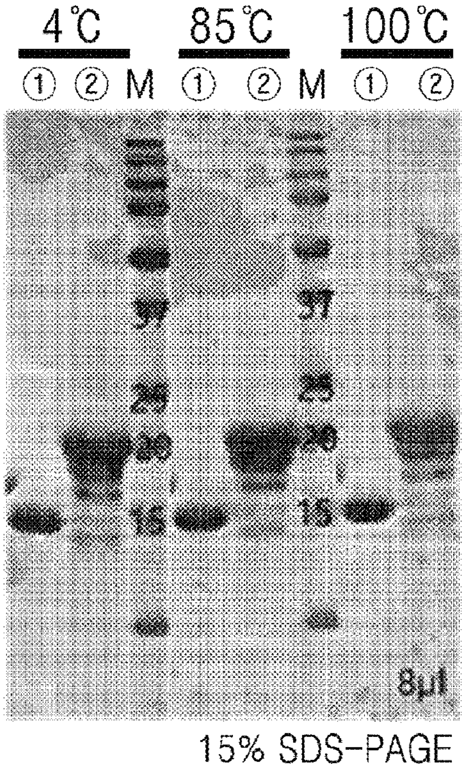
FIG. 4 is a diagram showing SDS-PAGE results after heat treatment of an FGF21 wild-type and an FGF21 terminal-truncation mutant 11 at various temperatures.

In addition, the variant 0, which is expected to have a β-trefoil main body structure (41-173aa), and an active terminal-truncated variant 2, which includes an interaction site between a receptor and a cofactor, were purified without heat treatment and then incubated at 85° C. and 100° C. for 10 minutes. As a result of SDS-PAGE analysis of the supernatant obtained by centrifugation after the heat treatment, it was confirmed that the band was similar to the band of proteins stored in ice before heat treatment (FIG. 4), and that in the case of having the β-trefoil body structure of FGF21 (41-173aa), the proteins did not precipitate even after heat treatment.

Figure 5:
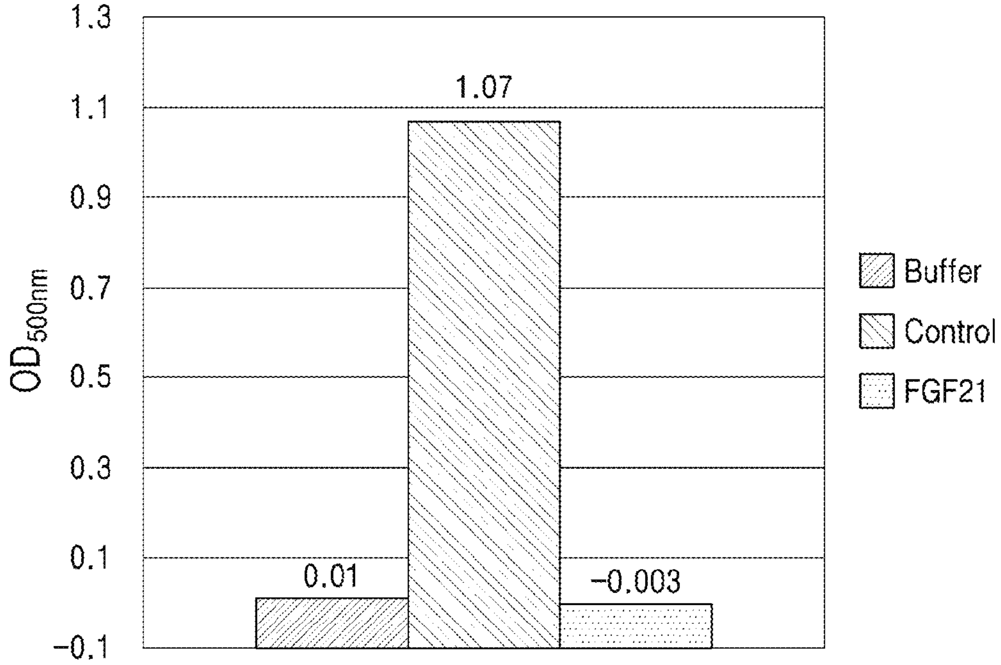
FIG. 5 is a view showing results of UV-visible spectroscopy after heat treatment of an FGF21 protein.

Next, the heat stability of the FGF21 protein was confirmed using a UV-Visible spectrometer. Specifically, when an OD500 of a solution containing the FGF21 (15 mg/ml, 41-173aa) that has been purified without heat treatment was measured after incubating the solution at 75° C. for 1 minute, it was confirmed that there was no change in the absorbance value (FIG. 5). Considering that the OD500 value of the control, which is a protein easily denatured by heat, increases when precipitation occurs at 75° C., it was confirmed that no precipitation occurred at 75° C. in the case of FGF21.

In addition, in the UV region (240 nm to 380 nm), the aggregation index $$\left(A.I. = \left(\frac{OD_{350\ nm}}{OD_{280\ nm} - OD_{350\ nm}}\right) \times 100\right)$$

was measured under three conditions (active state at 25° C./state at 75° C./re-cooling state after 1-hour heat treatment at 75° C.) for the FGF21 (15 mg/ml, 41-173aa) and the control protein solution vulnerable to heat. In the case of FGF21 having heat-elasticity, it was confirmed that the change in A.I. value was small and the graph patterns were very similar in the three conditions despite the heat treatment. Meanwhile, in the case of the control protein vulnerable to heat, the A.I. value was calculated as a relatively very high value of 176.3 at 75° C., and was measured as 106.6 even in a re-cooling state. In addition, it was confirmed that the graph pattern of the control protein was greatly changed by heat treatment and was not recovered even after re-cooling (FIG. 6). Based on these results, it was confirmed that the FGF21 has 'heat-elasticity' referring that it is denatured by heat treatment and recovers to an active structure upon re-cooling.

Figure 7:
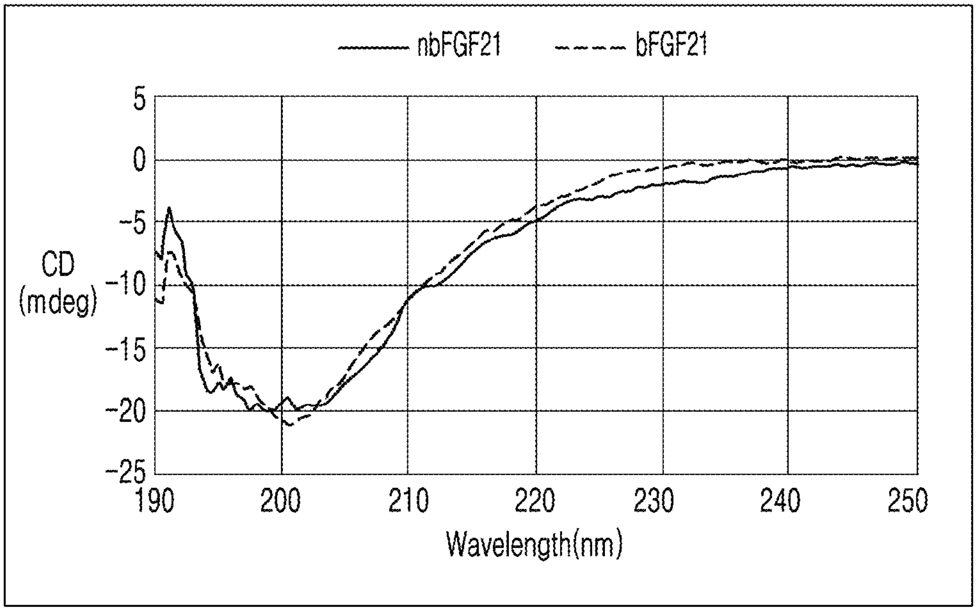
FIG. 7 is a diagram showing results of CD spectrum analysis of Far-UV region of an FGF21 protein.
Figure 8:
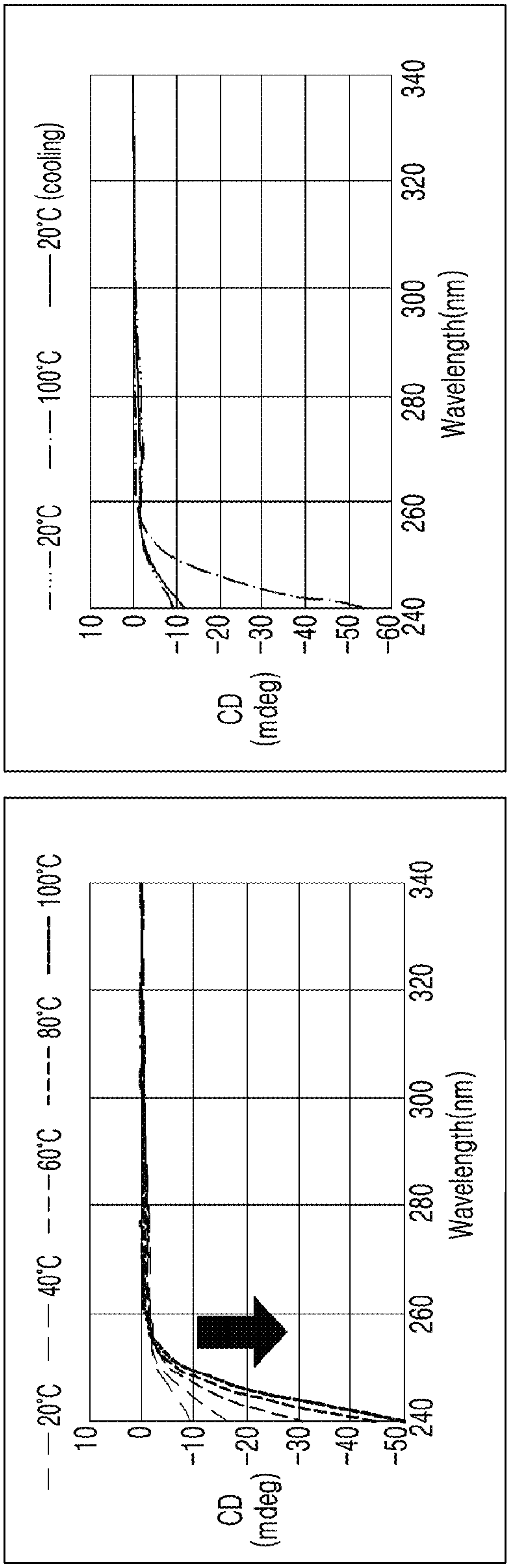
FIG. 8 is a diagram showing results of CD spectrum analysis of Near-UV region of an FGF21 protein.

The heat-elasticity of FGF21 was also confirmed in a circular dichroism (CD) experiment. In the Far-UV region (190 nm to 250 nm), which has a unique profile according to the secondary structure ratio of the protein, and in the Near-UV region (240 nm to 340 nm), which is sensitive to the structural change of the protein, changes in the CD spectrum of FGF21 according to temperatures were observed. Specifically, to confirm effects of the heat treatment on the structural changes of FGF21, FGF21 purified without heat treatment (i.e., non-boiled FGF21=nbFGF21, 29-209aa) and purified FGF21 after heat treatment (i.e., boiled FGF21=bFGF21, 33-209aa) were analyzed for the CD spectrum in the Far-UV region. Here, it was confirmed that the ratio of the secondary structure was maintained despite the heat treatment (at 100° C. for 10 minutes) based on the similarity of the CD spectra of nbFGF21 and bFGF21 (FIG. 7). In addition, the CD spectrum of bFGF21 in the near-UV region continuously changes as the temperature rises from 20° C. to 100° C., but after incubation at 100° C. for 5 minutes, the spectrum recovers to the pre-heat treatment spectrum as the temperature decreases to 20° C., thereby confirming the heat-elasticity (FIG. 8).

Summarizing the above results, it was confirmed that the FGF21 protein is not denatured even by performing heat treatment thereon, does not precipitate, and returns to the original structure when re-cooled after heat treatment, indicating that the FGF21 protein has excellent heat stability and heat-elasticity.

Example 2: Purification Method Using Heat-Elasticity of FGF21

Figure 9:
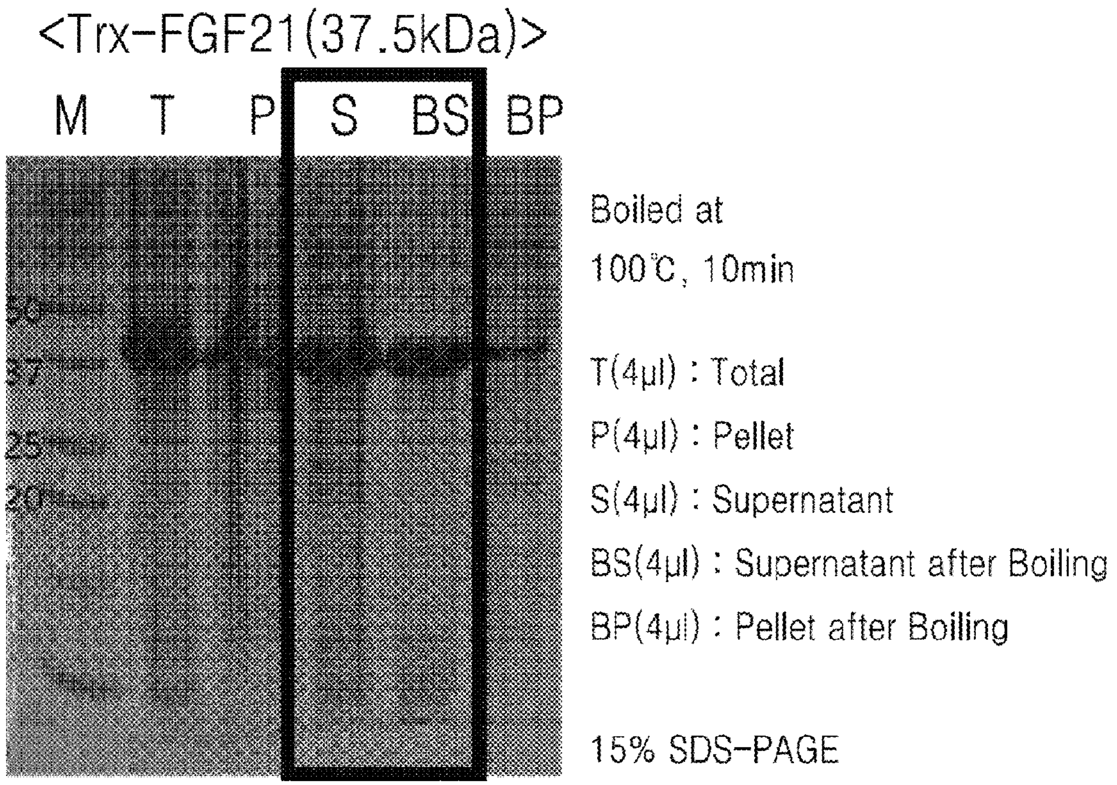
FIG. 9 is a diagram showing SDS-PAGE results after heat treatment of Trx-FGF21.

When the heat-elasticity of FGF21 confirmed in Example 1 is used in a protein purification process, a production process can be simplified and a production cost can be reduced. First, to increase the expression level of FGF21, a heat-resistant protein, such as thioredoxin (Trx) or Dnak, may be used as a tag. FGF21 fused with such a heat-resistant protein can be overexpressed in an *E. coli* system and purified through various chromatographic techniques. However, by introducing a heat treatment process, the protein purification process can be simplified. In detail, to purify/secure high-purity recombinant FGF21 (33-209aa) by using the heat-elasticity of FGF21, *E. coli* in which Trx-FGF21 consisting of FGF21 fused to Trx was overexpressed was disrupted by sonication, followed by centrifugation. The supernatant solution containing Trx-FGF21 was incubated at a high temperature (50° C. to 100° C.) for 10 minutes, and then proteins denatured at a high temperature and Trx-FGF21 were separated by centrifugation. Through SDS-PAGE analysis of samples at each stage, it was confirmed that Trx-FGF21 was present in a water-soluble state (FIG. 9).

Figure 10:
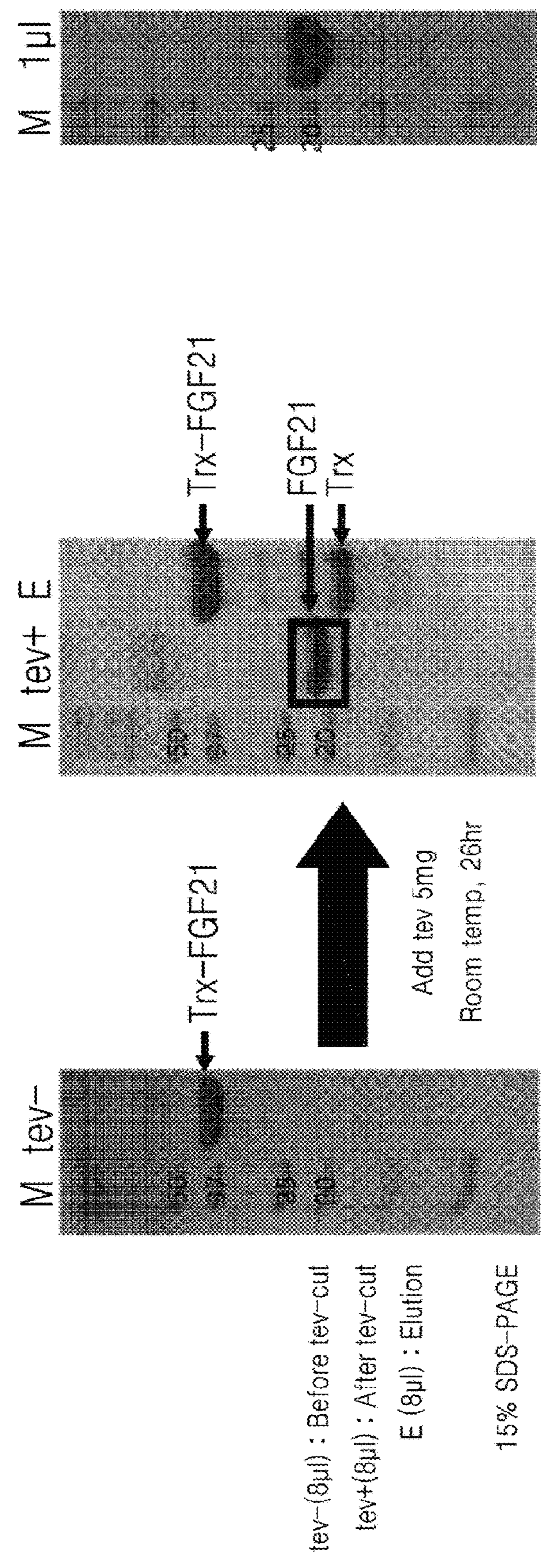
FIG. 10 is a diagram showing SDS-PAGE results at a purification process of Trx-FGF21 and a process of obtaining a final FGF21 protein.

In addition, to secure pure FGF21 from which Trx was removed, a cleavable linker must be inserted between the tag and FGF21. Specific sequences recognized by a tobacco etch virus (TEV)-derived protease or a protease such as thrombin and Factor Xa, etc. can be used as a linker, and it was confirmed that FGF21 can be isolated by using such linkers (FIG. 10). Therefore, FGF21 can be separated from the tag by a protease, and then purified with a high purity of 90% or more by using two or less chromatographic techniques. In addition, when an asparagine-glycine (Asn-Gly) linker is inserted between the tag and FGF21, the linker can be cleaved by heat treatment (40° C. to 42° C., 3 hours) by using hydroxylamine ($NH_2OH$).

Taken together, a protein purification process may include a heat treatment process when the excellent heat stability and elasticity of FGF21 are utilized, and accordingly, processes of removing impurities and other proteins can be simplified. By fusion with a heat-resistant protein tag to FGF21, there is an advantage of improving a production yield and the like.

Example 3: Confirmation of Physiological Activity of Heat-Treated FGF21

FGF21 exhibits various physiological effects by activating fibroblast growth factor receptor 1c isoform (FGFR1c), which is one of FGF receptors. Therefore, to confirm an effect of heat treatment on the activity of FGF21, the following experiment was performed.

Figure 11:
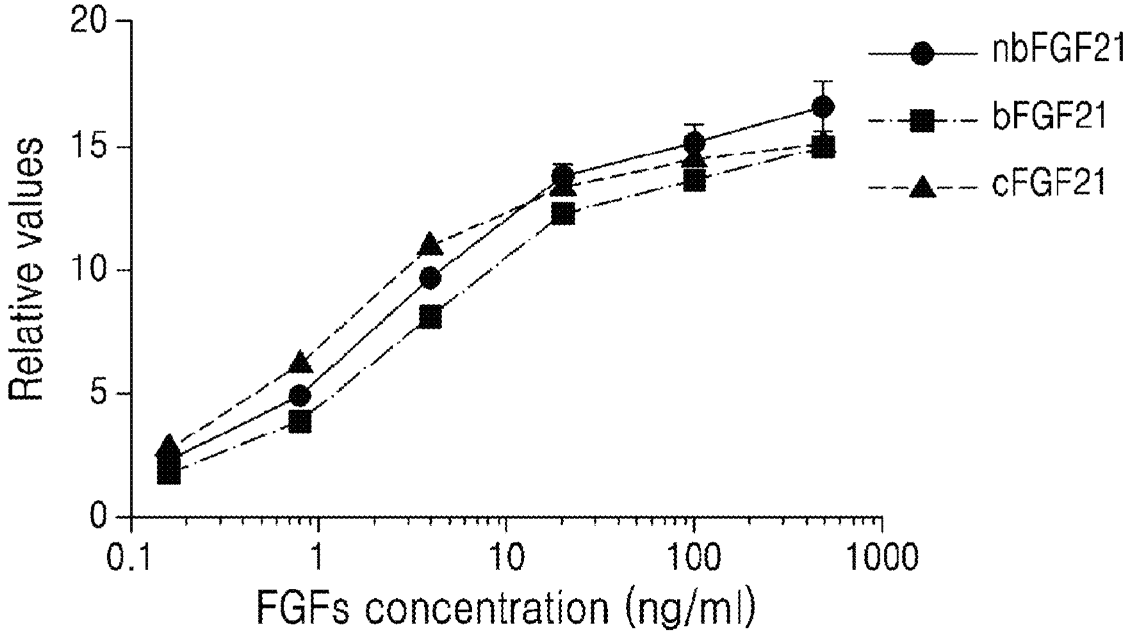
FIG. 11 is a diagram showing results of an experiment to confirm activation ability of a receptor by FGF21 protein depending on heat treatment.

In detail, the FGFR1c signaling ability of nbFGF21 (33-209aa), bFGF21 (33-209aa), and commercially available FGF21 (commercial FGF21=cFGF21, 29-209aa) was confirmed. For this, modified HEK293 cells (iLite FGF21 assay ready cells, Euro Diagnostica, Cat #BM3071) expressing FGFR1c and FGF receptor-binding cofactor, β-Klotho, and having a reporter system capable of confirming the degree of activation of FGFR1c were used. As a result of the experiment, it was confirmed that the receptor activation ability of bFGF21 was similar to that of nbFGF21 and cFGF21 (FIG. 11).

Figure 12:
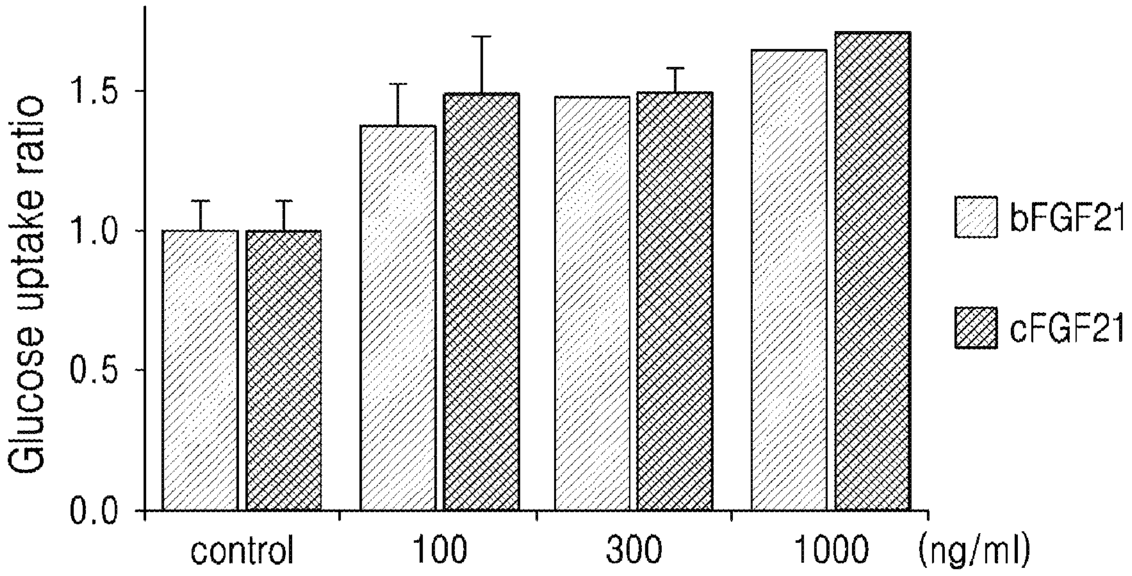
FIG. 12 is a diagram showing results of an experiment to confirm glucose transport ability by an FGF21 protein in a cell depending on heat treatment.

In addition, since FGF21 promotes glucose transport and has an activity to increase cellular glucose uptake, the glucose transport capability of heat-treated FGF21 was confirmed. In detail, to confirm the glucose transport ability, 2-deoxyglucose (2DG) was used. A glucose transporter that transports glucose into cells does not distinguish between glucose and 2DG, and 2DG absorbed into cells is phosphorylated in the same way as glucose to form 2-deoxyglucose-6-phosphate (2DG6P), but cannot proceed to the next step anymore. Thus, the degree of glucose transport ability can be confirmed by measuring the amount of 2DG6P. By using glucose Uptake-Glo assay (Promega, Cat #J1342), a which is product for confirming the amount of 2DG6P in cells using a luminometric method, and 3T3L1 adipocytes, which are mainly expressed by FGFR1c to which FGF21 binds, the glucose transport ability of FGF21 proteins was measured. As a result, it was confirmed that the activity of bFGF21 was similar to that of cFGF21 (FIG. 12).

Taken together, it was confirmed that, when the FGF21 protein was heat treated or re-cooled after heat treatment, the physiological activity of the FGF21 protein was the same/similar to that before heat treatment, and thus even when the FGF21 protein was produced/purified through a heat treatment process, there is no abnormality in the function of the FGF21 protein.

The foregoing descriptions are only for illustrating the disclosure, and it will be apparent to a person having ordinary skill in the art to which the disclosure pertains that the embodiments disclosed herein can be easily modified into other specific forms without changing the technical spirit or essential features. Therefore, it should be understood that Examples described herein are illustrative in all respects and are not limited. For example, each component described as in a single type may be implemented in a distributed manner, and likewise components described as being distributed may be implemented in a combined form.

The scope of the disclosure is indicated by the following claims rather than the detailed description above, and all changes or modifications derived from the meaning and scope of the claims and equivalent concepts thereof should be construed as being included in the scope of the disclosure.

The invention claimed is:

1. A method of producing an FGF21 protein, the method comprising:

a) culturing a transformant producing an FGF21 protein; and b) heating the transformant and/or its culture medium at a temperature of 65° C. or higher.

2. The method of claim 1, wherein the FGF21 protein comprises a wild type or a variant, and the wild type or variant comprises the amino acid sequence of SEQ ID NO: 2.

3. The method of claim 1, wherein the FGF21 protein has heat stability or heat-elasticity.

4. The method of claim 1, wherein the FGF21 protein has a β-trefoil structure.

5. The method of claim 1, wherein the FGF21 protein is additionally fused to a thermostable protein tag.

6. The method of claim 1, further comprises c) removing proteins denatured by heat treatment.

7. A method of purifying an FGF21 protein, the method comprising heating a mixture containing an FGF21 protein and impurities at a temperature of 65° C. or higher.

8. The method of claim 7, further comprising: removing proteins denatured by heat treatment.

* * * * *

SEQUENCE LISTING

```
<160> NUMBER OF SEQ ID NOS: 5

<210> SEQ ID NO 1
<211> LENGTH: 181
<212> TYPE: PRT
<213> ORGANISM: Artificial Sequence
<220> FEATURE:
<223> OTHER INFORMATION: human FGF_wild type, mature form
```

<400> SEQUENCE: 1

His Pro Ile Pro Asp Ser Ser Pro Leu Leu Gln Phe Gly Gly Gln Val
1 5 10 15

Arg Gln Arg Tyr Leu Tyr Thr Asp Asp Ala Gln Gln Thr Glu Ala His
20 25 30

Leu Glu Ile Arg Glu Asp Gly Thr Val Gly Gly Ala Ala Asp Gln Ser
35 40 45

Pro Glu Ser Leu Leu Gln Leu Lys Ala Leu Lys Pro Gly Val Ile Gln
50 55 60

Ile Leu Gly Val Lys Thr Ser Arg Phe Leu Cys Gln Arg Pro Asp Gly
65 70 75 80

Ala Leu Tyr Gly Ser Leu His Phe Asp Pro Glu Ala Cys Ser Phe Arg
85 90 95

Glu Leu Leu Leu Glu Asp Gly Tyr Asn Val Tyr Gln Ser Glu Ala His
100 105 110

Gly Leu Pro Leu His Leu Pro Gly Asn Lys Ser Pro His Arg Asp Pro
115 120 125

Ala Pro Arg Gly Pro Ala Arg Phe Leu Pro Leu Pro Gly Leu Pro Pro
130 135 140

Ala Leu Pro Glu Pro Pro Gly Ile Leu Ala Pro Gln Pro Pro Asp Val
145 150 155 160

Gly Ser Ser Asp Pro Leu Ser Met Val Gly Pro Ser Gln Gly Arg Ser
165 170 175

Pro Ser Tyr Ala Ser
180

<210> SEQ ID NO 2
<211> LENGTH: 133
<212> TYPE: PRT
<213> ORGANISM: Artificial Sequence
<220> FEATURE:
<223> OTHER INFORMATION: human FGF_N12C26

<400> SEQUENCE: 2

Gly Gly Gln Val Arg Gln Arg Tyr Leu Tyr Thr Asp Asp Ala Gln Gln
1 5 10 15

Thr Glu Ala His Leu Glu Ile Arg Glu Asp Gly Thr Val Gly Gly Ala
20 25 30

Ala Asp Gln Ser Pro Glu Ser Leu Leu Gln Leu Lys Ala Leu Lys Pro
35 40 45

Gly Val Ile Gln Ile Leu Gly Val Lys Thr Ser Arg Phe Leu Cys Gln
50 55 60

Arg Pro Asp Gly Ala Leu Tyr Gly Ser Leu His Phe Asp Pro Glu Ala
65 70 75 80

Cys Ser Phe Arg Glu Leu Leu Leu Glu Asp Gly Tyr Asn Val Tyr Gln
85 90 95

Ser Glu Ala His Gly Leu Pro Leu His Leu Pro Gly Asn Lys Ser Pro
100 105 110

His Arg Asp Pro Ala Pro Arg Gly Pro Ala Arg Phe Leu Pro Leu Pro
115 120 125

Gly Leu Pro Pro Ala
130

<210> SEQ ID NO 3
<211> LENGTH: 177

<212> TYPE: PRT
<213> ORGANISM: Artificial Sequence
<220> FEATURE:
<223> OTHER INFORMATION: human FGF_N4

<400> SEQUENCE: 3

Asp Ser Ser Pro Leu Leu Gln Phe Gly Gly Gln Val Arg Gln Arg Tyr
1 5 10 15

Leu Tyr Thr Asp Asp Ala Gln Gln Thr Glu Ala His Leu Glu Ile Arg
20 25 30

Glu Asp Gly Thr Val Gly Gly Ala Ala Asp Gln Ser Pro Glu Ser Leu
35 40 45

Leu Gln Leu Lys Ala Leu Lys Pro Gly Val Ile Gln Ile Leu Gly Val
50 55 60

Lys Thr Ser Arg Phe Leu Cys Gln Arg Pro Asp Gly Ala Leu Tyr Gly
65 70 75 80

Ser Leu His Phe Asp Pro Glu Ala Cys Ser Phe Arg Glu Leu Leu Leu
85 90 95

Glu Asp Gly Tyr Asn Val Tyr Gln Ser Glu Ala His Gly Leu Pro Leu
100 105 110

His Leu Pro Gly Asn Lys Ser Pro His Arg Asp Pro Ala Pro Arg Gly
115 120 125

Pro Ala Arg Phe Leu Pro Leu Pro Gly Leu Pro Pro Ala Leu Pro Glu
130 135 140

Pro Pro Gly Ile Leu Ala Pro Gln Pro Pro Asp Val Gly Ser Ser Asp
145 150 155 160

Pro Leu Ser Met Val Gly Pro Ser Gln Gly Arg Ser Pro Ser Tyr Ala
165 170 175

Ser

<210> SEQ ID NO 4
<211> LENGTH: 209
<212> TYPE: PRT
<213> ORGANISM: Artificial Sequence
<220> FEATURE:
<223> OTHER INFORMATION: human FGF21 wild-type (1-209 aa)

<400> SEQUENCE: 4

Met Asp Ser Asp Glu Thr Gly Phe Glu His Ser Gly Leu Trp Val Ser
1 5 10 15

Val Leu Ala Gly Leu Leu Leu Gly Ala Cys Gln Ala His Pro Ile Pro
20 25 30

Asp Ser Ser Pro Leu Leu Gln Phe Gly Gly Gln Val Arg Gln Arg Tyr
35 40 45

Leu Tyr Thr Asp Asp Ala Gln Gln Thr Glu Ala His Leu Glu Ile Arg
50 55 60

Glu Asp Gly Thr Val Gly Gly Ala Ala Asp Gln Ser Pro Glu Ser Leu
65 70 75 80

Leu Gln Leu Lys Ala Leu Lys Pro Gly Val Ile Gln Ile Leu Gly Val
85 90 95

Lys Thr Ser Arg Phe Leu Cys Gln Arg Pro Asp Gly Ala Leu Tyr Gly
100 105 110

Ser Leu His Phe Asp Pro Glu Ala Cys Ser Phe Arg Glu Leu Leu Leu
115 120 125

Glu Asp Gly Tyr Asn Val Tyr Gln Ser Glu Ala His Gly Leu Pro Leu
130 135 140

-continued

```
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 5
<211> LENGTH: 152
<212> TYPE: PRT
<213> ORGANISM: Artificial Sequence
<220> FEATURE:
<223> OTHER INFORMATION: human FGF21 wild-type_N12C17 (41-192 aa)

<400> SEQUENCE: 5

Gly Gly Gln Val Arg Gln Arg Tyr Leu Tyr Thr Asp Asp Ala Gln Gln
1               5                   10                  15

Thr Glu Ala His Leu Glu Ile Arg Glu Asp Gly Thr Val Gly Gly Ala
            20                  25                  30

Ala Asp Gln Ser Pro Glu Ser Leu Leu Gln Leu Lys Ala Leu Lys Pro
        35                  40                  45

Gly Val Ile Gln Ile Leu Gly Val Lys Thr Ser Arg Phe Leu Cys Gln
    50                  55                  60

Arg Pro Asp Gly Ala Leu Tyr Gly Ser Leu His Phe Asp Pro Glu Ala
65                  70                  75                  80

Cys Ser Phe Arg Glu Leu Leu Leu Glu Asp Gly Tyr Asn Val Tyr Gln
                85                  90                  95

Ser Glu Ala His Gly Leu Pro Leu His Leu Pro Gly Asn Lys Ser Pro
            100                 105                 110

His Arg Asp Pro Ala Pro Arg Gly Pro Ala Arg Phe Leu Pro Leu Pro
        115                 120                 125

Gly Leu Pro Pro Ala Leu Pro Glu Pro Pro Gly Ile Leu Ala Pro Gln
    130                 135                 140

Pro Pro Asp Val Gly Ser Ser Asp
145                 150
```